US008425039B2

(12) United States Patent
Gonzalez de la Rosa

(10) Patent No.: US 8,425,039 B2
(45) Date of Patent: Apr. 23, 2013

(54) PERIMETRIC METHOD

(75) Inventor: Manuel Gonzalez de la Rosa, Santa Cruz de Tenerife (ES)

(73) Assignee: Oculus Optikgeraete GmbH, Wetzlar-Dutenhofen (DE)

(*) Notice: Subject to any disclaimer, the term of this patent is extended or adjusted under 35 U.S.C. 154(b) by 215 days.

(21) Appl. No.: 13/035,320

(22) Filed: Feb. 25, 2011

(65) Prior Publication Data
US 2011/0205493 A1  Aug. 25, 2011

(30) Foreign Application Priority Data

Feb. 25, 2010 (EP) ..................... 10154707
Oct. 29, 2010 (EP) ..................... 10189429

(51) Int. Cl.
*A61B 3/02* (2006.01)
(52) U.S. Cl.
USPC .......................... 351/224; 351/246
(58) Field of Classification Search .......... 351/222–224, 351/237, 246
See application file for complete search history.

(56) References Cited

U.S. PATENT DOCUMENTS

| 4,813,779 | A | 3/1989 | Schneider et al. |
| 5,050,983 | A | 9/1991 | Johnson et al. |
| 5,565,949 | A | 10/1996 | Kasha, Jr. |
| 5,864,385 | A | 1/1999 | Gonzales de la Rosa |
| 7,367,674 | B2 | 5/2008 | Kirchhuebel |
| 7,377,646 | B2 * | 5/2008 | Suzuki ................ 351/224 |
| 2003/0223038 | A1 | 12/2003 | Alster et al. |
| 2008/0312552 | A1 | 12/2008 | Zhou et al. |
| 2009/0073387 | A1 | 3/2009 | Meyer et al. |
| 2010/0249532 | A1 | 9/2010 | Maddess et al. |

FOREIGN PATENT DOCUMENTS

| EP | 1340451 A2 | 9/2003 |
| JP | 2007-319407 | 12/2007 |
| JP | 2007-319408 | 12/2007 |
| WO | 2009/059380 A1 | 5/2009 |
| WO | 2009/073970 A1 | 6/2009 |

OTHER PUBLICATIONS

Search Report issued in corresponding EP Application No. 10 18 9429, completed on Jun. 16, 2011 and mailed on Jun. 28, 2011.
Imaging and Perimetry Society webpages, downloaded Feb. 14, 2011, from http://webeye.ophth.uiowa.edu.
Yasuyuki Suzuki: The Sector Analysis for a Visual Field, Neuro-opthalmology, vol. 15, No. 3; no translation available, submitted for certification purposes only, (1998).
Tappe, Hartmut, Patent Attorney—Letter dated Mar. 7, 2013.

* cited by examiner

*Primary Examiner* — Huy K Mai
(74) *Attorney, Agent, or Firm* — Griffin & Szipl, P.C.

(57) ABSTRACT

The invention relates to a perimetric method for measuring a visual field of an eye, carried out with an ophthalmological device, particularly a perimeter or similar device, and an apparatus for data processing provided with a data base, wherein the data base includes data sets of visual fields, wherein a retina of the eye is divided into points that represent the visual field, wherein the points of the retina are exposed to optical stimuli of a defined intensity, wherein a reaction to a stimulus is calculated as a measurement result, wherein at least two predefined points are measured, wherein the predefined points each lie in anatomically independent nerve fiber regions and are in a statistically significant relation to each other, wherein a visual field of the eye is derived from the measurement results and the data sets.

20 Claims, 15 Drawing Sheets

$D26=(0.1\times D12)+(0.5\times D16)+(0.05\times D38)+(0.1\times D52)+(0.2\times D55)+(0.1\times D65)$

PERIMETRIC METHOD

This application claims priority from European Patent Application No. 10154707.3, filed Feb. 25, 2010, and from European Patent Application No. 10189429.3, the entire disclosures of which are incorporated herein by reference.

FIELD OF THE INVENTION

The invention relates to a perimetric method for measuring the visual field of an eye.

BACKGROUND OF THE INVENTION

Perimetric methods are regularly used to determine the visual field of an eye, and, accordingly, of the person being examined. An eye's visual field may be limited as a result of a disease of the eye, for example, glaucoma, wherein the glaucoma may progress to complete loss of vision. The cause of vision loss may also be a disease of the optic nerve or damage to the nerve fibres (nerve fibers). The nerve fibres in the eye may be divided into various nerve fibre regions of a retina, all of which lead to the optic nerve (optic disc) and the "blind spot", where no photoreceptor cells are located.

In a perimetric examination of an eye's visual field, the patient's eye is exposed to optical stimuli, and the patient signals whether the given stimulus was detected or not. Thus, perimeters are known in which a patient looks into a hemisphere, via which the points of light are projected in different positions and at various levels of brightness under the control of a computer program. In this way, it is possible to examine both the overall extent of a visual field and the condition of selected regions thereof. The brightness of the points of light may be varied in such manner that a threshold value above which the patient detects the point of light can be determined for a position on the retina.

Various methods for determining visual fields and threshold values are known from the related art. In essence, a series of stimuli with various gradations of brightness are directed at a point on the retina to be measured or tested, so that the specific threshold value for the point may be determined. In order to localise a threshold value, this may be carried out with uniform or non-uniform gradations, for example. Additionally, a data base containing representative thresholds for a number of persons may be incorporated. In this way, for example, a possible threshold value may be delimited within a threshold range taking into account a patient's age and sex. It is also known that there is a relationship between directly adjacent regions or measurement points in the retina. Thus, for example, threshold values typically do not differ substantially between neighbouring points. Accordingly, if a threshold value has been determined for a first point, a threshold value for a directly adjacent point may be sought within a probable threshold value range. Accordingly, the overall advantage of such a method is that a patient has to be exposed to fewer stimuli and a visual field may be determined more quickly.

It should also be noted that a large number of stimuli does not necessarily result in more accurate results when determining a visual field, since it is quite normal for persons undergoing examination to feel the effects of neurological retinal fatigue or tiredness while their visual field is being measured, thereby distorting the results of the examination. Accordingly, several tests or measurements of a visual field may also be carried out at different times in order to counter the effects of fatigue. Consequently, it is generally desirable to determine a visual field using a number of stimuli that enables the time for measuring the visual field to be kept as brief as possible, so that the effect of fatigue does not cause any significant distortion of a measurement result. At the same time, the requirement exists to measure a visual field as accurately as possible, and for this a large number of stimuli is necessary.

The underlying object of the present invention is, therefore, to provide a perimetric method for measuring the visual field of an eye that yields sufficiently accurate measurement results with a relatively small number of stimuli.

BRIEF SUMMARY OF THE INVENTION

This object of the invention is solved with a perimetric method having the features of a first embodiment, which pertains to a perimetric method for measuring a visual field of an eye, carried out with an ophthalmological device, such as a perimeter or similar device, and an apparatus for data processing provided with a data base, wherein the data base includes data sets of visual fields, wherein a retina of the eye is divided into points (21) that represent the visual field, wherein the points of the retina are exposed to optical stimuli of a defined intensity, wherein a reaction to a stimulus is calculated as a measurement result, wherein at least two predefined points (P12, P16, P38, P52, P55, P65) are measured, wherein the predefined points each lie in anatomically independent nerve fibre regions (11, 12, 13, 14,15, 16) and are in a statistically significant relation to each other, wherein a visual field of the eye is derived from the measurement results and the data sets. In accordance with a second embodiment of the invention, the first embodiment is modified so that the measured results of the measured predefined points (P12, P16, P38, P52, P55, P65) are compared with the data sets for respectively matching points that are stored in the data base, wherein a visual field of an eye is derived from the data sets that are revealed by the comparison to approximately match the measured results. In accordance with a third embodiment of the present invention, the first embodiment and the second embodiment are further modified so that a difference between the measured results for the predefined points (P12, P16, P38, P52, P55, P65) and the measured results stored in the data base for matching points of the data sets is used as a comparison criterion in the comparison.

In accordance with a fourth embodiment of the present invention, the first embodiment, the second embodiment, and the third embodiment, are further modified so that the predefined points (P12, P16, P38, P52, P55, P65) are selected from the data base. In accordance with a fifth embodiment of the present invention, the first embodiment, the second embodiment, the third embodiment, and the fourth embodiment, are further modified so that the predefined points (P12, P16, P38, P52, P55, P65) are located at a distance from each other.

In accordance with a sixth embodiment of the present invention, the first embodiment, the second embodiment, the third embodiment, the fourth embodiment, and the fifth embodiment are further modified so that a predefined first point (P52, P55) is measured using a first stimulus, wherein an intensity of another, second stimulus is determined for a predefined, further, second point (P12, P16) depending on the result of measurement of the preceding point, wherein subsequently the second point is measured using the second stimulus. In accordance with a seventh embodiment of the present invention, the sixth embodiment is further modified so that an intensity of the further stimulus is calculated by including the measurement results contained in the data sets that are expected for the subsequent point (P12, P16). In accordance with an eighth embodiment of the present invention, the sixth embodiment or the seventh embodiment is further modified so that one of two possible intensities is selected depending on the preceding measurement result.

In accordance with a ninth embodiment of the present invention, the first embodiment, the second embodiment, the third embodiment, the fourth embodiment, the fifth embodiment, the sixth embodiment, the seventh embodiment and the eighth embodiment are further modified so that a point (21) is measured using a single stimulus. In accordance with a tenth embodiment of the present invention, the first embodiment, the second embodiment, the third embodiment, the fourth embodiment, the fifth embodiment, the sixth embodiment, the seventh embodiment and the eighth embodiment are further modified so that a point (21) is measured by a sequence of stimuli having differing intensities. In accordance with an eleventh embodiment of the present invention, the first embodiment, the second embodiment, the third embodiment, the fourth embodiment, the fifth embodiment, the sixth embodiment, the seventh embodiment, the eighth embodiment, the ninth embodiment, and the tenth embodiment, are further modified so that a third and a fourth predefined point (P16, P55) is measured in a similar manner to the first and second points (P12, P52). In accordance with a twelfth embodiment of the invention, the eleventh embodiment is further modified so that one of the four predefined points (P12, P16, P38, P52, P55, P65) may be measured again depending on the results of its own measurement and the measurement of a preceding point (P12, P16, P52, P55).

In accordance with a thirteenth embodiment of the present invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, and the twelfth embodiment, are further modified so that a further predefined point (P12, P16, P38, P52, P55, P65) is measured depending on the measurement results of two preceding points (P12, P16, P38, P52, P55). In accordance with a fourteenth embodiment of the present invention, the thirteenth embodiment is further modified so that a further predefined point (P65) is measured on the basis of the measured results of all preceding points (P12, P16, P38, P52, P55). In accordance with a fifteenth embodiment of the present invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, and the fourteenth embodiment are further modified so that additional measurable points (21) are measured in a first measurement phase (A) following the predefined points (P12, P16, P38, P52, P55, P65). In accordance with a sixteenth embodiment of the present invention, the fifteenth embodiment is further modified so that all measurable points (21) are jointly measured in three further measurement phases (B, C, D), wherein a visual field for the eye is derived from the median obtained from the measured results from all measurement phases. In accordance with a seventeenth embodiment of the present invention, the fifteenth embodiment and the sixteenth embodiment are further modified so that one optical stimulus having a defined intensity is applied to each predefined point (P12, P16, P38, P52, P55, P65) before the first measurement phase (A), wherein the measurement result is then used to determine the intensity of the subsequent optical stimuli of the first measurement phase (A).

More generally, the perimetric method of the invention for measuring the visual field of an eye is carried out using an ophthalmological device, particularly a perimeter or similar device, and using means for data processing provided with a data base, wherein the data base includes data sets of visual fields, wherein a retina of the eye is divided into points that have corresponding points in the visual field respectively that represent the visual field, wherein the points of the retina are exposed to optical stimuli of a defined intensity, wherein a reaction to a stimulus is calculated as a measurement result or test result, wherein at least two predefined points are measured, wherein the predefined points lie in anatomically independent nerve fibre regions and are in a statistically significant relationship to each other, wherein a visual field of the eye is derived from the measurement results and the data sets.

Within the scope of the method according to the invention, a first predefined point on the retina is subjected to a stimulus. A response to the stimulus by the person—stimulus detected/stimulus not detected—defines the measurement and test result for this point, taking into account the intensity of the stimulus. At this point, particularly the detected/not detected response by the person is always referred to as a measurement or measurement result, because it always leads to a measurement result in the overall result, or in the case of a single measurement may represent a measurement result on its own. It is assumed at the start of measurement of the visual field that the predefined points to be measured are known measurement points.

The method according to the invention is based on the underlying idea that a statistical relationship exists between the points on the retina defined by measurement results that are not directly adjacent one another, just as there is for points that are directly adjacent one another. In this context, the characterizing feature of the method of the invention is that the points, whose statistical relationship is considered, each lie in nerve fibre regions that are anatomically independent of each other. Measurement of predefined points that are located in the same nerve fibre region within the retina is avoided because this would increase the number of stimuli required. According to the method of the present invention, nerve fibre regions are differentiated particularly on the basis of functional relationships that define a nerve fibre region. The definitions of nerve fibre regions known from the prior art refer to a morphological definition of these regions.

The statistical link between the predefined points is based on a probability of a relationship between these points. For example, a threshold value or threshold value range of a second predefined point may be assigned to a threshold value of a first predefined point with a high degree of probability. The data sets of visual fields contained in the data base each include the predefined points that are in a relationship with measurement results of other predefined points based on a significantly high correlation of the measurement results of a predefined point. However, in order to carry out the method it is not absolutely essential to determine the predefined points from the data base, since they are known from experience anyway. The predefined points may thus be considered to be fixed points, which are measured as the first points in the context of the method.

Following the measurement of the first predefined point, the second predefined point is measured by applying a stimulus. Since these two points are statistically related, as was explained above, it is possible to deduce a visual field from the measurement results of the two points that, with a high degree of probability, is actually present given these measurement results. For this purpose, the data base, which contains a large number of visual fields, is used, and a visual field matching the measurement results in question is generated as a concluding measurement result of the method. In this way, it is possible to obtain highly accurate measurement results using a very small number of stimuli, and thereby avoid the errors in measurement that are attributable to fatigue.

The general objective of the invention is to shorten examination time much more that the current strategies, so that it can be repeated and averaged, thus providing much more stable results, reducing fluctuation and thus facilitating follow up. Stable results are contributing to define more precise normality patterns and more reproducible results. It is then easier to differentiate pathology from normality and stability from progression.

The determination of a visual field as a measurement result may be performed particularly simply by comparing the measured results of the measured predefined points with the data sets for matching points that are stored in the data base, wherein the field of vision of an eye is derived from the data sets that are revealed by the comparison to approximately match the measured results.

Comparison of the measured results with the data sets may be improved further if a difference between the measured results for the predefined points and the measured results stored in the data base for matching points of the data sets is used as a comparison criterion in the comparison. For example, a threshold value difference between the measured values of the predefined points compared with the actual, stored measured results or threshold values allows a local deviations to be deducted for the purposes of an expected measured result of a subsequent, prescribed point. In order to determine the local deviation of an expected threshold value, regression analysis or some similar approach may be used.

It is also possible to adopt the predefined points not as fixed points that were defined before the start of the method, but to make a selection of the predefined points from the data base. In this way, the data base may serve to identify the predefined points that are always needed as part of the method, and to specify them in a first step of the method. Any change in the data base may thus also affect the selection of predefined points.

In addition, the predefined points may be located at a distance from each other. This means that the predefined points are no longer located directly adjacent each other, but they are clearly separated from each other by points that are located between them. A relative distance between the predefined points may be comparatively large, with the result that predefined points are distributed relatively evenly over a visual field. Therefore, the employed statistical relationship between predefined points may also exist for points that are widely separated. For example, a relative distance between the predefined points may be over 50% of a length of a straight line expressed as a ratio of a spatial extent of the vision field in the range of the straight line.

In an advantageous embodiment of the method, a predefined first point may be measured with a first stimulus, wherein an intensity of another, second stimulus may be determined for a predefined, further, second point depending on the result of measurement of the preceding point, wherein subsequently the second point may be measured by means of the second stimulus. Therefore, the stimulus intended for the second point may be selected following analysis of the measurement result of the first point depending on the first measurement result. The data base may be used to calculate the second stimulus and a measurement range for the second predefined point, in which a threshold value may be expected with a high degree of probability. In this way, it is possible to restrict a possible threshold value range for the second predefined point, with the advantageous result that a smaller number of stimuli overall is required to determine the threshold values.

An intensity of the second stimulus may also be calculated using the measurement results contained in the data sets that are probably to be expected for the second point. In general, a standard deviation may be considered in all calculations of expected measurement results, or of threshold values, or of threshold value ranges.

The method may be further simplified if one or two possible intensities are selected depending on the preceding measurement result. This means, if for example a stimulus having a given intensity in a predefined point was detected by patients, a second predefined point is measured using a stimulus having the first intensity. If the previous stimulus was not detected, a second intensity is used for the next predefined point. The choice of which of the two intensities is used is thus always dependent on the response to the preceding point. In this context, a magnitude of the two possible intensities may be derived from a probability of an expected threshold value of the subsequent point, as was explained earlier.

In order to keep the number of possible stimuli as low as possible, it may be intended to measure a point using a single stimulus. This means that measurement of the point is completed after only a single stimulus has been applied, and that this may be followed by measurement of a further point. Accordingly, there is then no provision to use a sequence of stimuli for the measurement in a method step defined as measurement.

Alternatively, in contrast thereto, a point may be measured using a sequence of stimuli having different intensities. This enables a threshold value to be defined even more closely, for example. According to this definition of a measurement within the scope of the method, at least two consecutive stimuli are used to measure a point. Of course, it is also conceivable to mix individual stimuli and stimulus sequences for the respective measurement of points.

In a further embodiment of the method, a third or fourth predefined point may be measured in a similar manner to the first and second points. Increasing the number of predefined points does enable more accurate results to be obtained when the visual field is derived.

In addition, one of the four predefined points may be measured again depending on the results of its own measurement and of a preceding point. In this way, a possible threshold range of the point in question may be defined yet more closely taking into account the preceding results. In this way, is it possible to obtain an even more accurate result with a small number of stimuli.

It may also be provided that a further predefined point is measured depending on the measurement results of two preceding points. This means that the measurement results of two points are used to measure a predefined point that has not been measured before, and to adjust a stimulus intensity according to the measurement results. For example, a fifth predefined point may be measured taking into account the measured results of the first and third predefined point.

In a possible subsequent method step, a further predefined point may be measured on the basis of the measured results of all preceding points. For example, all final measurement results of the preceding points may be considered when measuring a sixth predefined point and when selecting a corresponding stimulus. In this way, the reliability of a result may be increased further still.

In order to obtain a relatively accurate reading and result with regard to a visual field, additional measurable points may be measured in a first measurement phase following the predefined points. By definition, the points following the predefined points are not fixed points, which means that these points may be selected essentially at will or depending on the measurement results of the predefined points. The points following the predefined points are thus not necessarily specified at the start of the method; instead, they may be determined during the course of the method. The additional points in question may originate from nerve fibre regions that are independent of each other. In the first measurement phase, all other additional points may also be measured, or also just some of the other points. A result of the first measurement phase may be a derivation of a visual field from the measured results of the predefined and the additional points.

The method may consist of up to four measurement phases, wherein altogether all measurable points are measured in three further measurement phases, wherein a visual field for the eye is derived from an average obtained from the measured results from all measurement phases. Therefore, one visual field is derived from each measurement phase, and the final result may be a visual field that has been averaged from the four visual fields of the measurement phases. This approach is advantageous if it is necessary to make allowance for the effects of fatigue on the persons being examined.

An optical stimulus having a defined intensity may also be applied to a predefined point before the first measurement phase, wherein the measurement result may then be used to determine the intensity of the subsequent optical stimuli of the first measurement phase. In this way, it is possible to define an assumed threshold value even more closely, thus simplifying the method further. For example, the measurement result may be used to identify or to estimate significant defects in the retina. Other subsequent measurements of points may then be omitted or simplified as required.

The method according to the invention may be performed using a perimeter or other such device, wherein the perimeter then includes means for processing data connected with a data base. Possible advantageous embodiments of a perimeter of such kind will be apparent in the descriptions of the features in the method embodiments.

The present invention will now be explained in greater detail with reference to the accompanying drawing.

BRIEF DESCRIPTION OF THE DRAWINGS

In the drawings:
FIG. 9: is the dot matrix of FIG. 1 with one method step;
FIG. 10: is the dot matrix of FIG. 7 with a further method step;
FIG. 11: is the dot matrix of FIG. 10 with a further method step;
FIG. 12: is the dot matrix of FIG. 11 with a further method step;
FIG. 13: is the dot matrix of FIG. 12 with a further method step.

DETAILED DESCRIPTION OF THE INVENTION

In the following passages, a possible workflow of the perimetric method will be described with reference to FIGS. 1 to 14.

Figure 1:
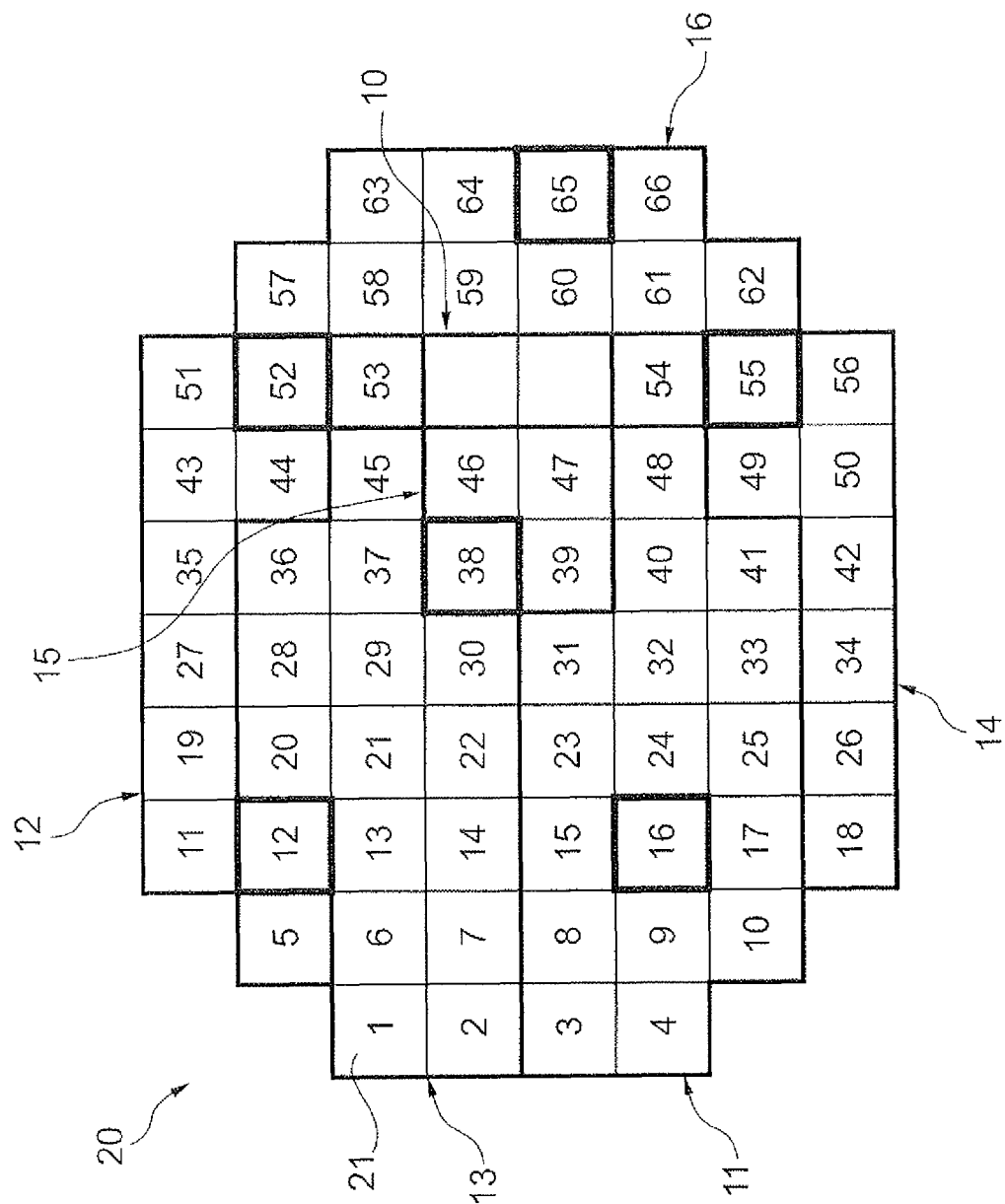
FIG. 1: is a dot matrix representing a visual field.

In general, any dot matrix may be used to carry out the method. FIG. 1 shows one possible dot matrix 20, representing a measurable visual field of a retina, which is not shown here. This means that stimuli are applied to an eye in the form of points of light of defined intensity via a perimeter in such manner that a stimulus may be allocated to one of the points 21 defined in dot matrix 20 and representing several regions of nerves. Points 21 are identified with numbers 1 to 66 in dot matrix 20 to enable them to be differentiated more easily. Where reference is made to one of the points 21 in the following, the format "Pnn" will be used to indicate which point is meant.

Dot matrix 20 is divided into six nerve fibre regions 11 to 16, these nerve fibre regions together represent a retina and separately represent different functional aspects. A zone 10 of dot matrix 20 represents an "optic nerve papilla", that is to say a blind spot in the visual field. Points P12, P16, P38, P52, P55, and P65 are predefined points, that is to say points 21 that have been defined as fixed points.

According to the method workflow, it is intended first to measure points P52 and P12 in nerve fibre regions 12 and 13 with four stimuli, then to measure points P55 and P16 in nerve fibre regions 14 and 11 with four stimuli, and finally to measure points P38 and P65 in nerve fibre regions 15 and 16 with two stimuli. The intensity of a subsequent stimulus in this sequence of stimuli is always determined on the basis of a possible threshold deviation of this stimulus. In general, the threshold values considered are corrected for the age and/or sex of the person being examined.

Figure 2:
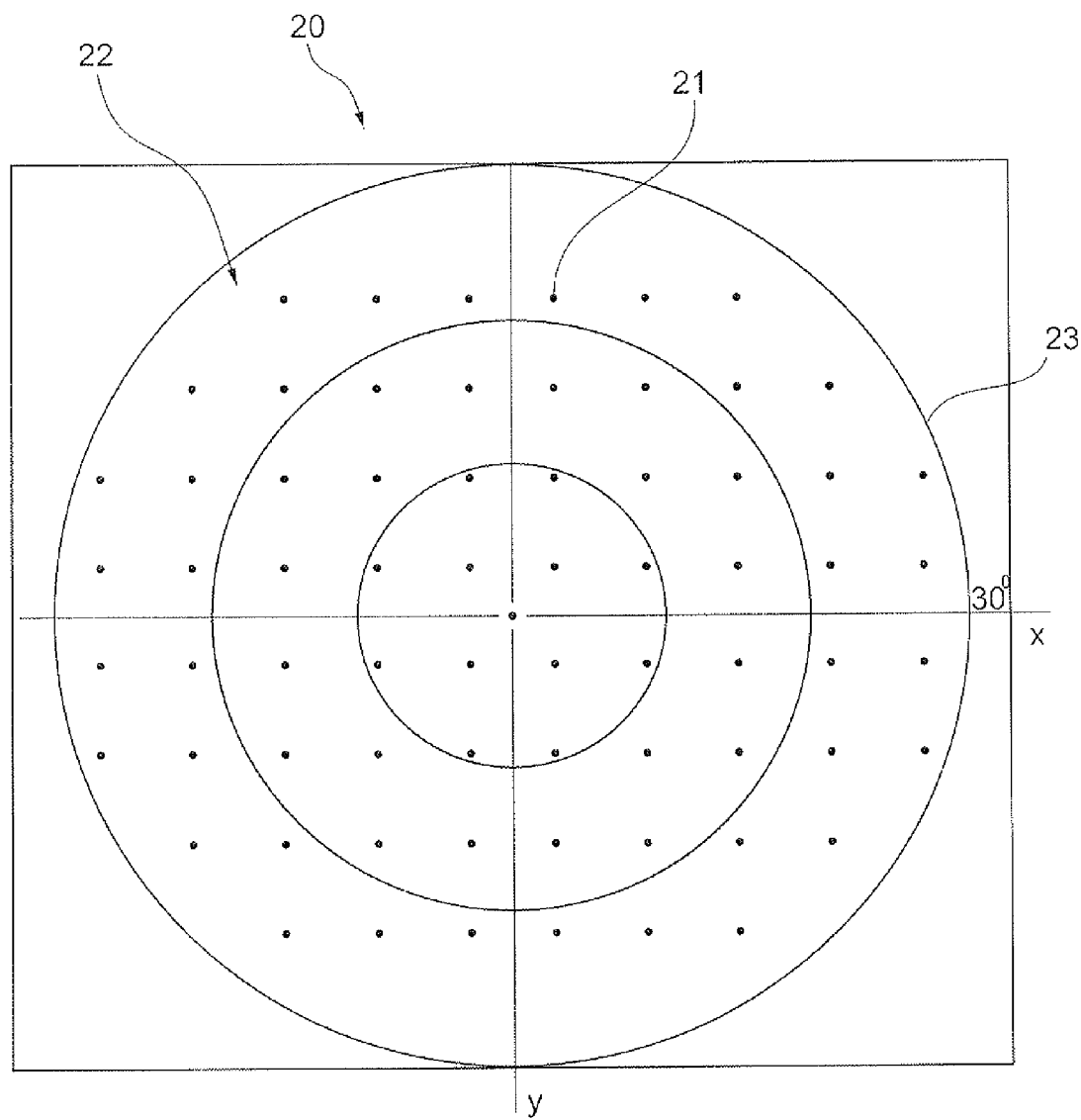
FIG. 2: is a dot matrix from the viewpoint of a patient.
Figure 3:
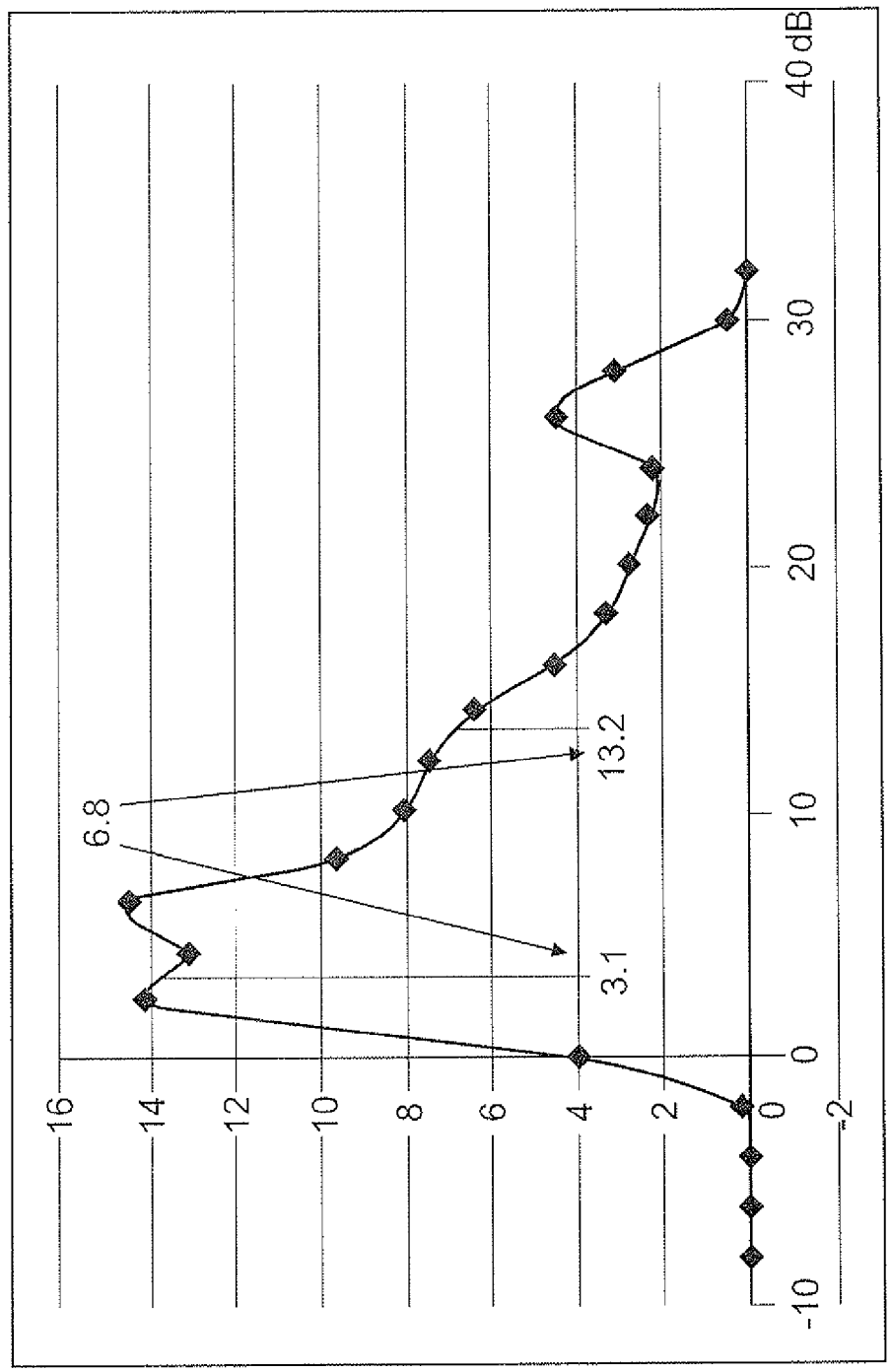
FIG. 3: is a frequency distribution plot of a deviation from age-adjusted threshold values for a point.

FIG. 2 is a representation of a dot matrix 20 of a perimeter, not further shown, from the viewpoint of a patient. A test zone 22 consists of 68 points 21, which form an orthogonal pattern inside a 30° arc 23. A horizontal and a vertical separation between adjacent points 21 corresponding to 6° in each case. Points 21 are arranged symmetrically about the X and Y axes, and no points lie directly on the X or Y axes. The maximum eccentricity of points 21 is +/−27° horizontally and +/−21° vertically.

Figure 4:
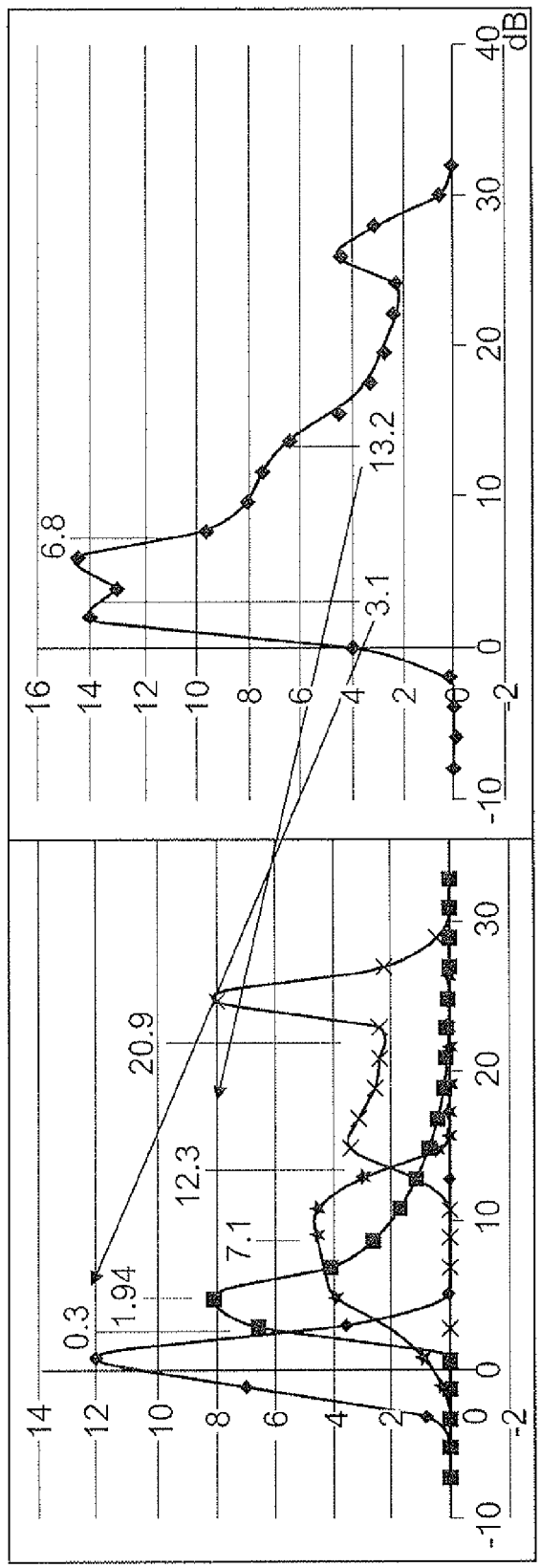
FIG. 4: is the plot of FIG. 3 with a plot of a further point.

FIGS. 3 to 8 each show frequency distribution plots of a deviation from the age-adjusted threshold value in a point 21. In this case, a stimulus intensity is expressed as a logarithmic value in decibels (dB) for the sake of simplicity. As may be seen by reviewing FIGS. 3 to 5 together, a measurement for point P52 is performed with a first stimulus having intensity 6.8 dB above the normal threshold value. A response—seen or not seen—enables a possibly deviation of a threshold value in this point to be calculated −3.1 dB for seen and 13.2 dB for not seen. Point P55 is measured in the same way with a second stimulus, that is to say in accordance with FIG. 6 with an intensity of 5.4 dB above the normal threshold value and possible results of 1.8 or 11.8 dB for seen and not seen respectively. Point P12 is now measured with a third stimulus as shown in FIG. 4 having an intensity of 1.94 or 12.3 dB above the normal threshold value based on the measurement result for point P52.

Figure 5:
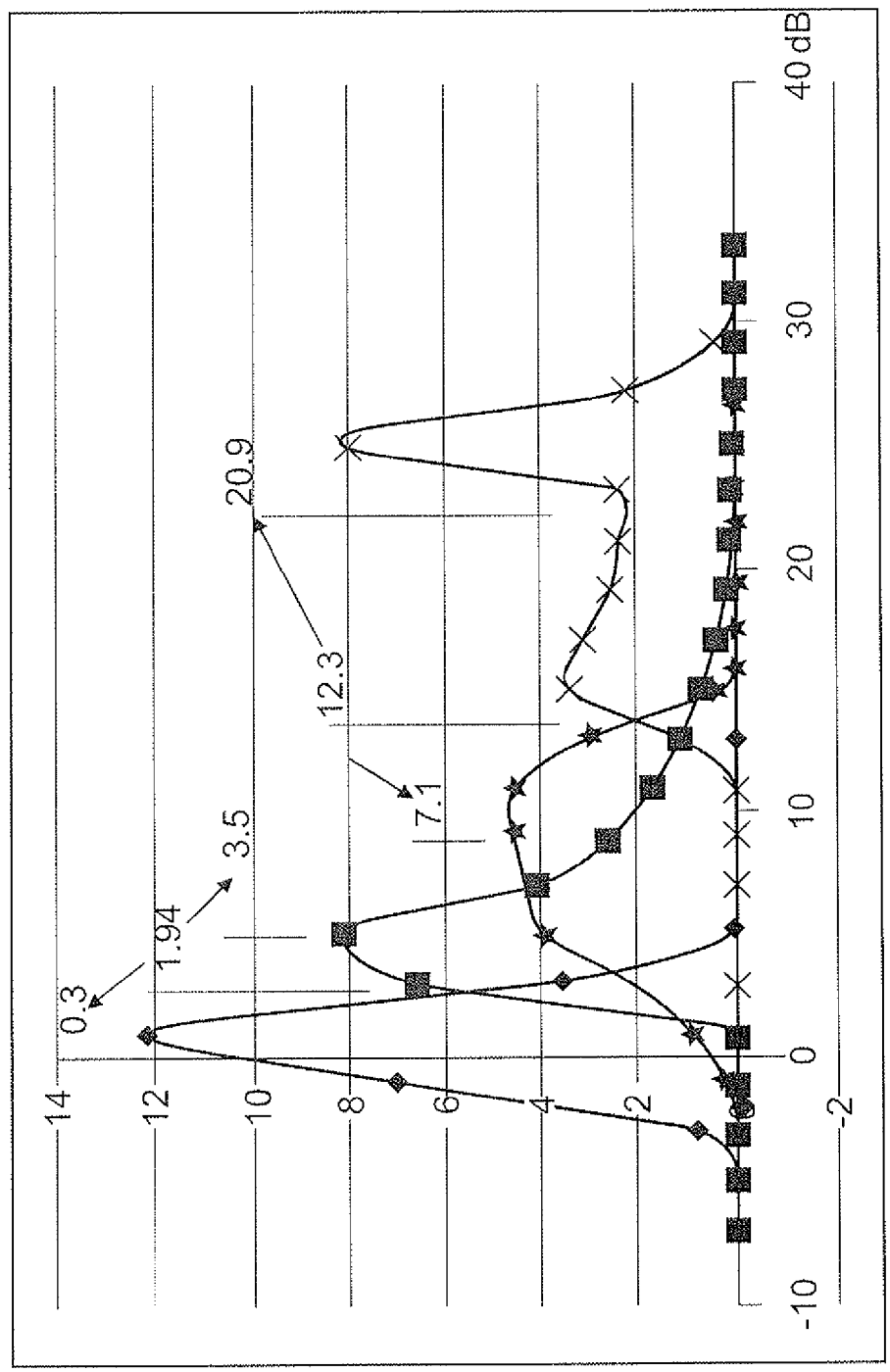
FIG. 5: is the plot of the further point from FIG. 4.
Figure 6:
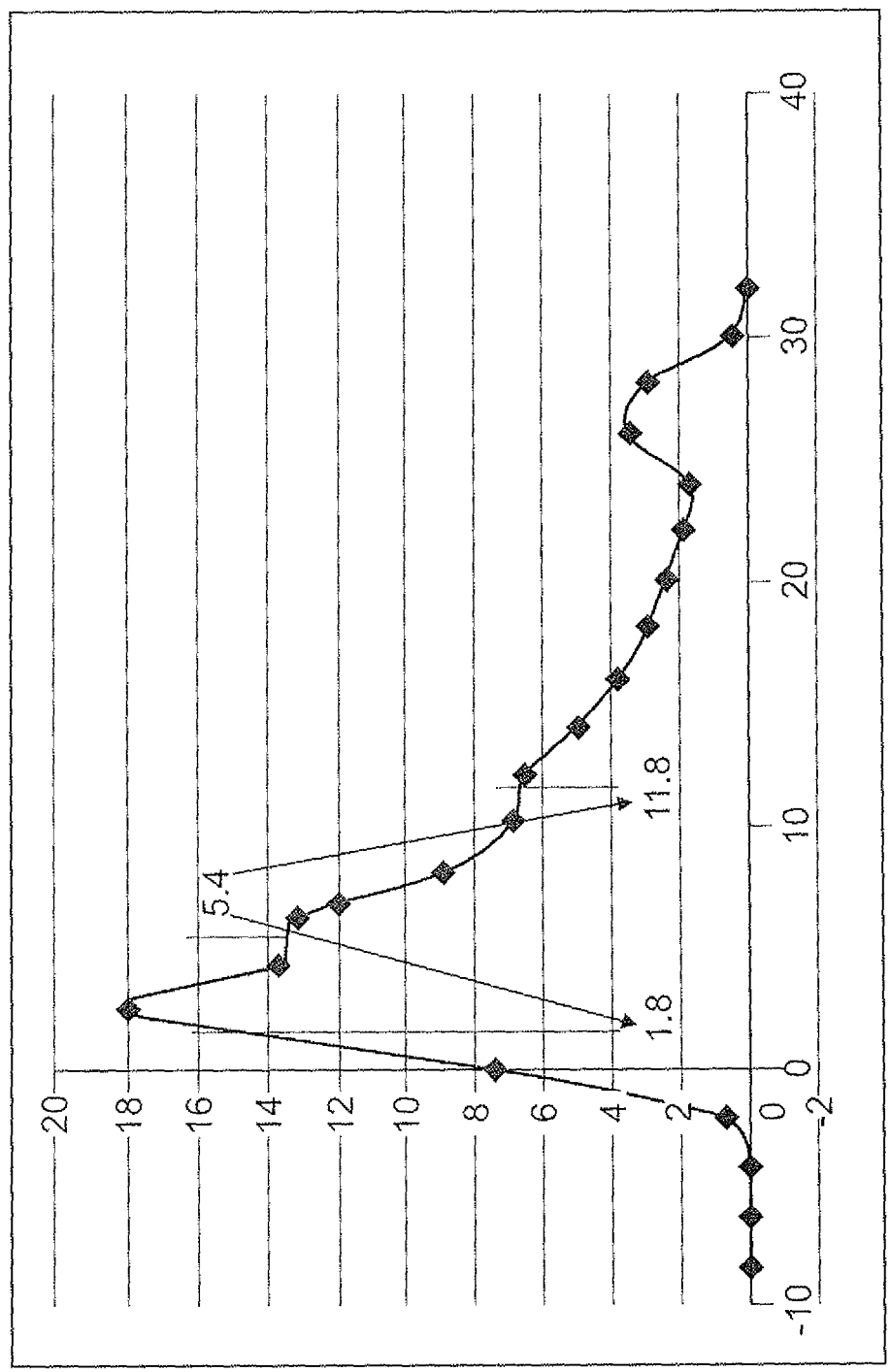
FIG. 6: is a plot of a frequency distribution of a deviation from age-adjusted threshold values for a point.
Figure 7:
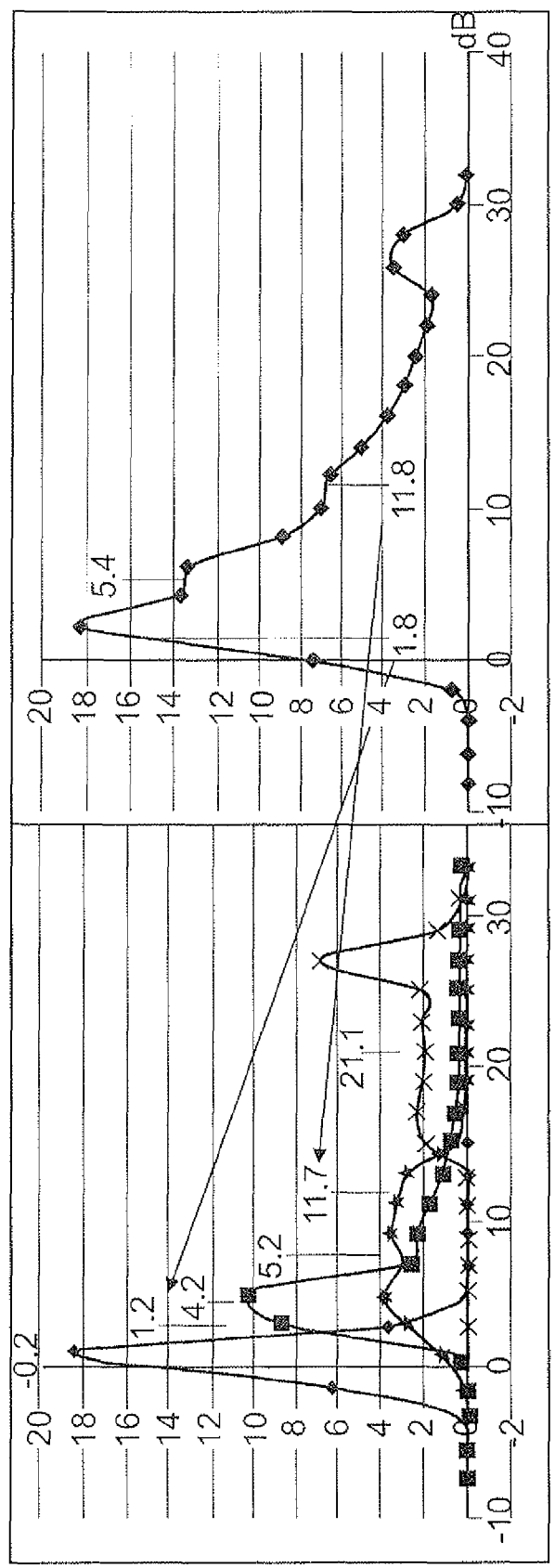
FIG. 7: is the plot of FIG. 6 with a plot of a further point.
Figure 8:
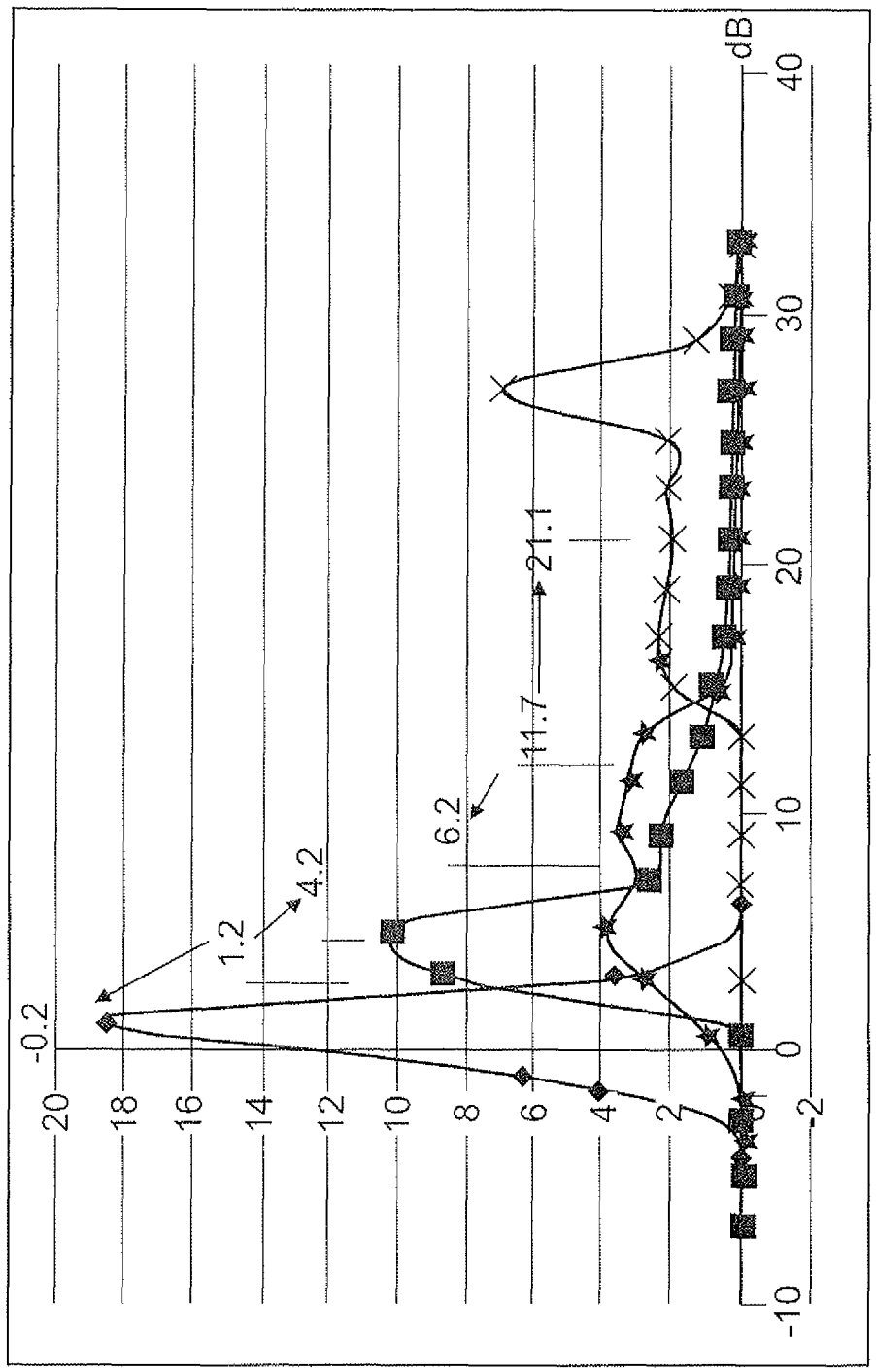
FIG. 8: is the plot of the further point from FIG. 7.

FIGS. 5 and 8 each show a plot with four possible frequency distributions. If, as shown in FIG. 5, the intensity of the stimulus is 1.94 dB above the normal threshold value, the result of the measurement is 0.3 above the normal threshold value if it is seen and 3.5 dB above if it is not seen. If the stimulus is 12.3 dB above the normal threshold value, the result of measurement is 7.1 dB if the stimulus is detected and 20.9 dB if the stimulus is not detected. The same procedure is followed with a fourth stimulus for point P16, as shown in the plots of FIGS. 7 and 8, each depending on the result for point P55.

Accordingly, these method steps result in four possible results each for points P12 and P16. The person being examined may thus initially be classified in one of sixteen groups with the corresponding specific frequency distribution for the threshold value in the points 21 that have been measured up to this time.

Figure 9:
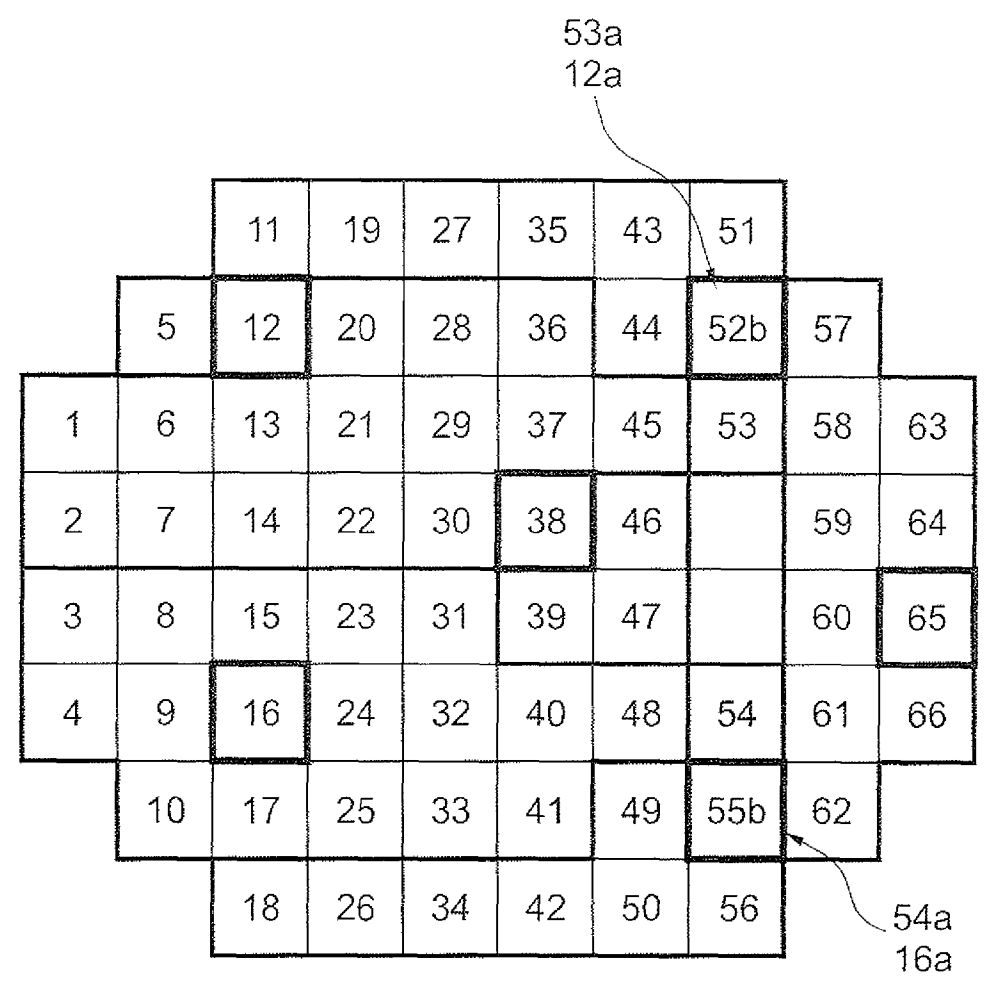
Figure 10:
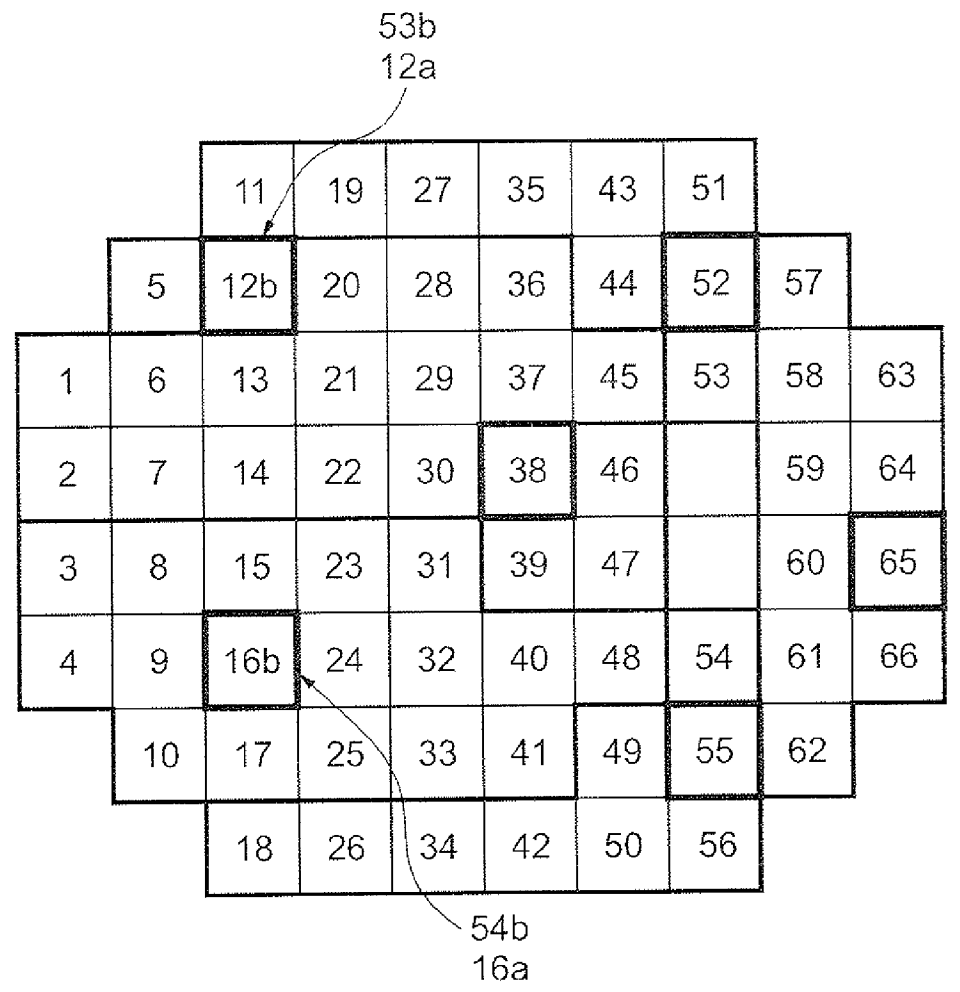

As is indicated in FIG. 9, point P52 is measured with a fifth stimulus, wherein a new intensity is calculated for the fifth stimulus on the basis of the results for points P52 and P12. In the same way, point P55 is calculated again after a sixth stimulus has been applied. As shown in FIG. 10, a seventh stimulus is then applied to point P12, in which case an intensity of the seventh stimulus is also recalculated on the basis of the preceding result for point P12 and the recalculated result for point P52. The procedure is repeated in the same way for point P16 using an eighth stimulus.

Figure 11:
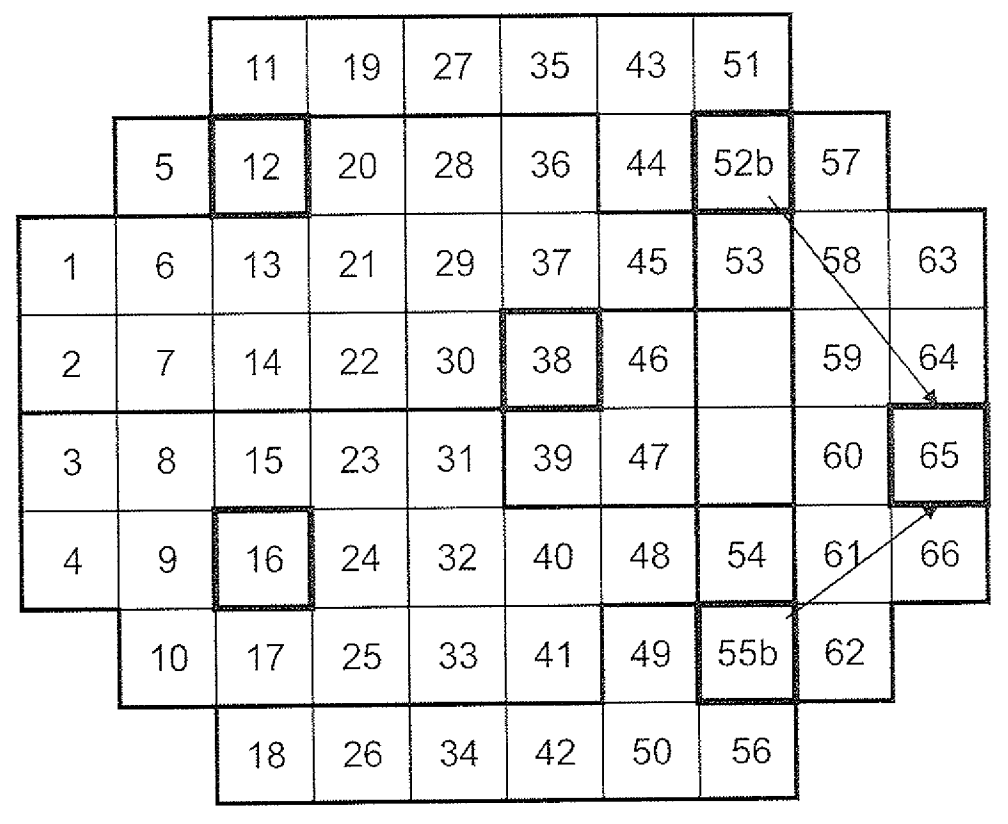
Figure 12:
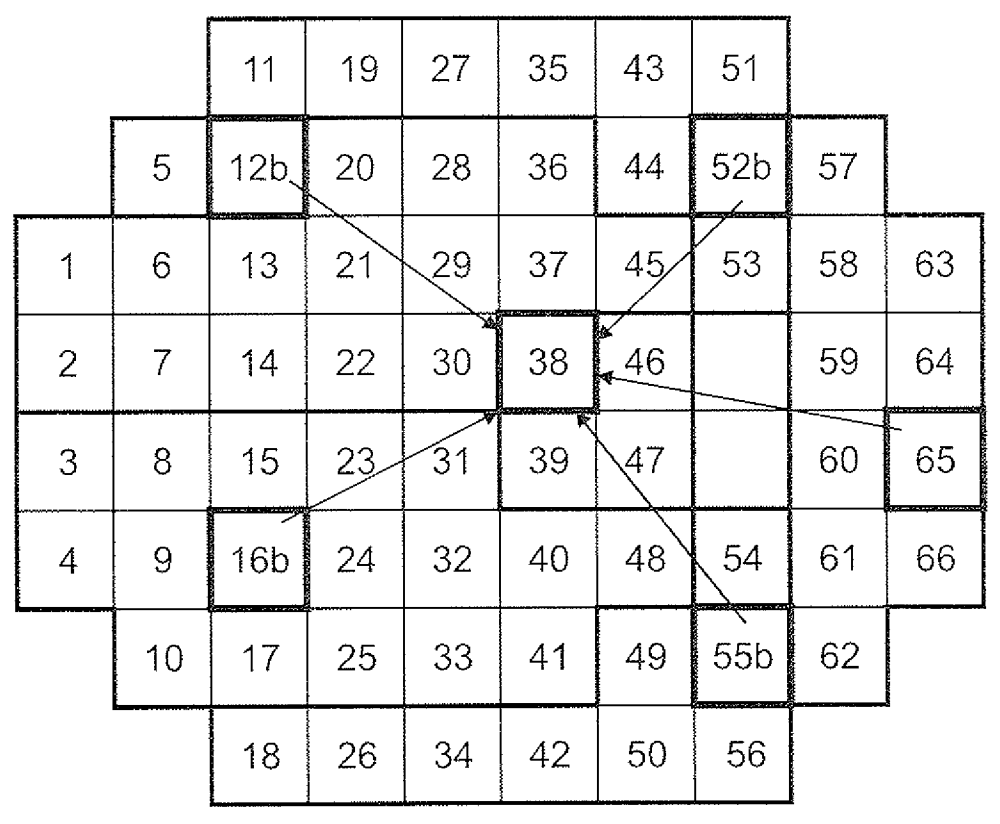

The results from points P52 and P55 enable an intensity for a ninth stimulus to be calculated for point P65, as is shown in FIG. 11, and finally point P38 is measured with a tenth stimulus. An intensity of the tenth stimulus is derived from the results of all preceding points P12, P52, P65, P55 and P16 as shown in FIG. 12. The examination takes 20 to 30 seconds for the ten stimuli.

Figure 14:
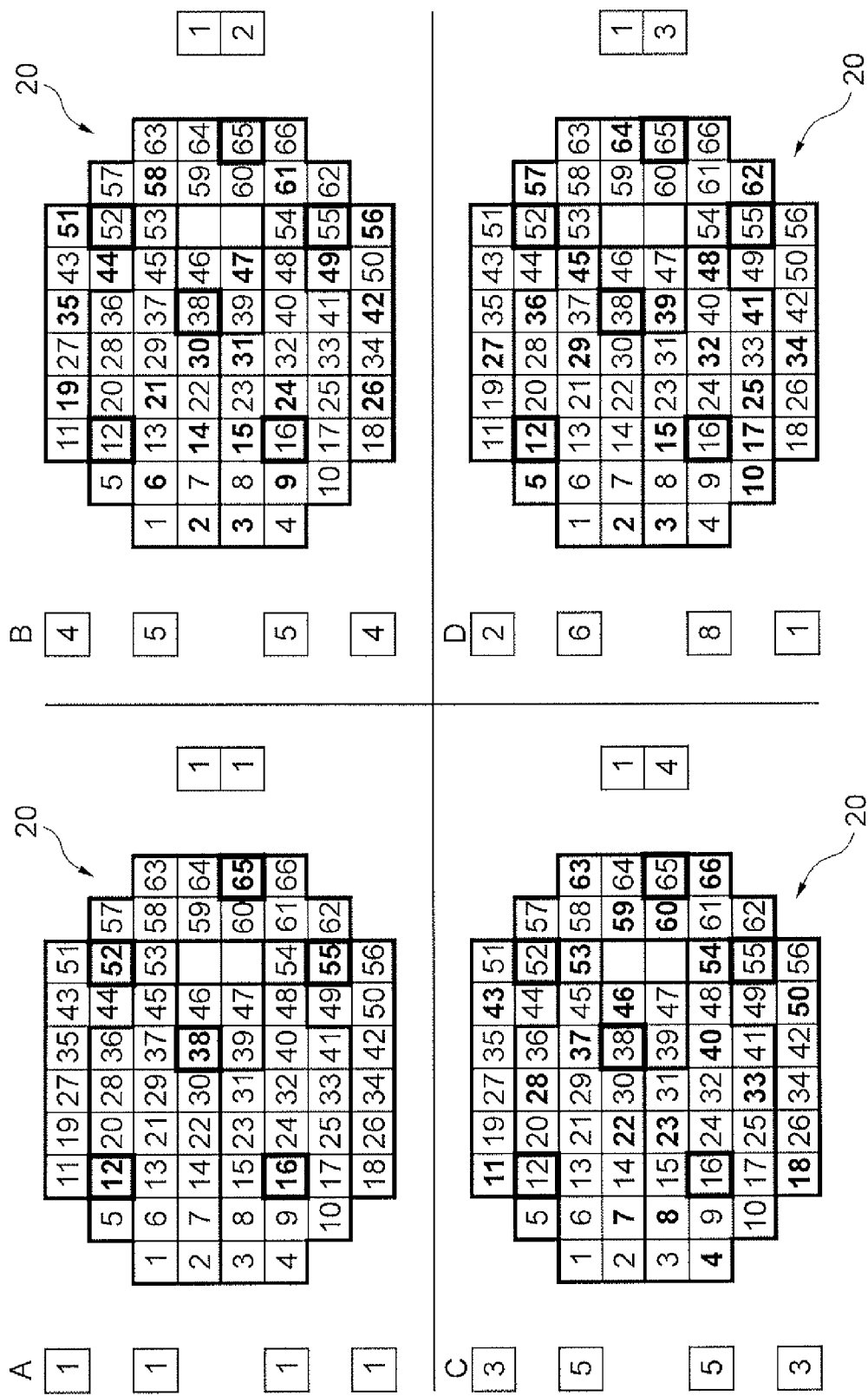
FIG. 14: is a representation of measurement phases using dot matrices.
Figure 15:
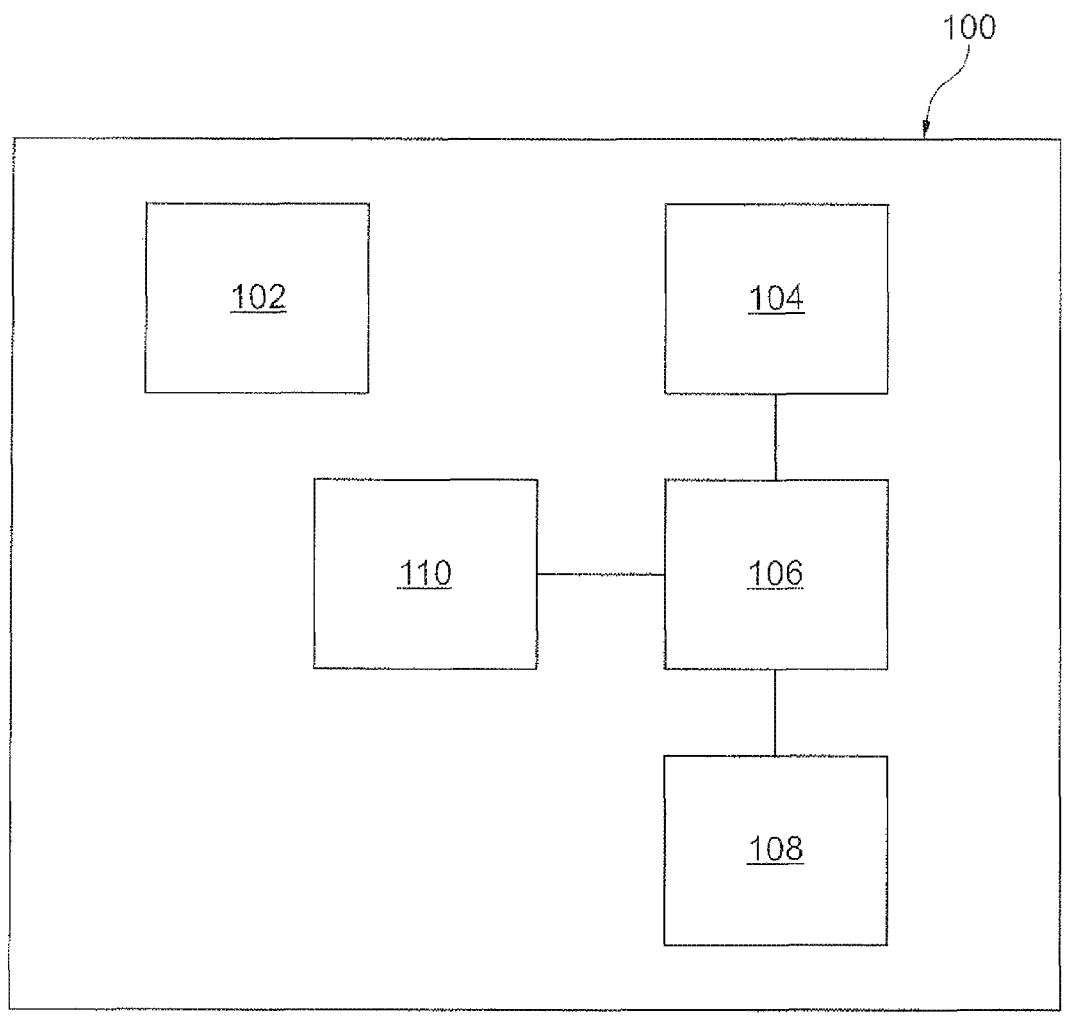
FIG. 15: is a schematic drawing of an ophthalmological device that is used to perform the perimetric method of the invention.

Finally, a maximum of the defects for all points 21 that have not yet been measured is estimated on the basis of the measurements for the six predefined points 21 using a regression analysis. To complete the first measurement phase, as shown in FIGS. 13 and 14, further points 21 are measured using the results of the predefined points 21. As may be seen in the dot matrix 20 for a first measurement phase, indicated by A in FIG. 14, one predefined point 21 is measured in each of the nerve fiber regions 11 to 16. Each of the measured points 21 are identified here by a bolded figure. In the second measurement phase, identified with the letter B, five points 21 are measured in nerve fiber region 11, four are measured in nerve fiber region 12, five in nerve fiber region 13, four in nerve fiber region 14, one in nerve fiber region 15, and two in nerve fiber region 16. In the subsequent third and fourth measurement phases, identified with the letters C and D respectively, all of the other points 21 are measured. In this way, it is also possible to draw conclusions regarding possible significant defects, which might be underestimated if only a few points were considered. FIG. 15 is a schematic of an ophthalmological device 100, such as a perimeter, that includes a light stimulus apparatus 102 that provides optical stimuli of a defined intensity, and a reaction measuring apparatus 104 that is disposed to measure a reaction by the test subject's eye to the optical stimulus provided by the light stimulus apparatus 102. Examples of perimeters that include a light stimulus apparatus and a reaction measuring apparatus are disclosed by U.S. Pat. No. 4,813,779 issued to Schneider et al., and U.S. Pat. No. 5,565,949 issued to Kasha, Jr., and U.S. Pat. No. 7,367,674 issued to Kirchhuebel, and all three of these patents are incorporated herein by reference for all they disclose. The ophthalmological device 100 also includes an apparatus 106 for data processing (i.e., a data processor and/or computer) operably connected with a data base 108. The data base 108 contains data sets of visual fields. The data processing apparatus 106 is operably connected to receive measured reaction data from the reaction measuring apparatus 104, which the data processing apparatus 106 uses to calculate the reaction of the test subject's eye to a stimulus as a measurement result. The data processing apparatus 106 uses one or more measurement results to calculate out a representation of a visual field, which may be outputted for display by a display apparatus 110. Thus, the opthalmological device 100 shown in FIG. 15 is a device that performs the perimetric method of the present invention, which measures the visual field of an eye of a test subject.

In sum then, the invention relates to a perimetric method for measuring a visual field of an eye, carried out with an ophthalmological device, particularly a perimeter or similar device, and with means for data processing with a data base, wherein the data base includes data sets of visual fields, wherein a retina of the eye is divided into points (21) that represent the visual field, wherein the points of the retina are exposed to optical stimuli of a defined intensity, wherein a reaction to a stimulus is calculated as a measurement result, wherein at least two predefined points (P12, P16, P38, P52, P55, P65) are measured, wherein the predefined points each lie in anatomically independent nerve fiber regions (11, 12, 13, 14,15, 16) and are in a statistically significant relation to each other, wherein a visual field of the eye is derived from the measurement results and the data sets.

The invention claimed is:

1. A perimetric method for measuring a visual field of an eye, wherein the perimetric method is carried out with an ophthalmological device that comprises an apparatus for data processing that is connected with a data base, wherein the data base includes data sets of visual fields, wherein the method comprises the steps of:
   (a) dividing a retina of the eye into points that represent the visual field of the eye;
   (b) exposing the points of the retina that represent the visual field to optical stimuli of a defined intensity;
   (c) using the apparatus for data processing to calculate a reaction to the optical stimuli as a measurement result, wherein at least two predefined points are measured, wherein the at least two predefined points each lie in anatomically independent nerve fibre regions and are in a statistically significant relation to each other; and
   (d) deriving a measured visual field of the eye from the measurement result calculated by the apparatus for data processing and from the data sets of the data base.

2. The method as recited in claim 1, further comprising the step of:
   (e) comparing one or more measurement results of the measured at least two predefined points with the data sets for respectively matching points that are stored in the data base, wherein the measured visual field of the eye is derived from the data sets that are revealed by the comparison to approximately match the one or more measurement results.

3. The method as recited in claim 2, wherein a difference between the measurement results for the at least two predefined points and second measurement results stored in the data base for matching points of the data sets is used as a comparison criterion in the comparison of step (e).

4. The method as recited in claim 1, wherein the at least two predefined points are selected from the data base.

5. The method as recited in claim 1, wherein the at least two predefined points are located at a distance from each other.

6. The method as recited in claim 1, wherein the at least two predefined points include a predefined first point and a predefined second point, wherein the predefined first point is measured using a first stimulus, and wherein an intensity of a second stimulus is determined for the predefined second point depending on the result of measurement of the preceding predefined first point, wherein subsequently the predefined second point is measured using the second stimulus.

7. The method as recited in claim 6, wherein the intensity of the second stimulus is calculated by including a second measurement result contained in the data sets that are expected for the subsequent predefined second point.

8. The method as recited in claim 7, wherein intensity of the second stimulus is selected from one of two possible intensities depending on the measurement result of the preceding predefined first point.

9. The method as recited in claim 6, wherein a predefined third point and a predefined fourth point are is measured in a similar manner to the predefined first point and the predefined second point.

10. The method as recited in claim 9, wherein a first one of the predefined first point, the predefined second point, the predefined third point and the predefined fourth point is selected to be measured again depending on the results of the measurement of the selected point and the measurement of a preceding point.

11. The method as recited in claim 10, wherein a second one of the predefined first, the predefined second point, the predefined third point and the predefined fourth point is measured again depending on the measurement results of two preceding points, wherein the first one is a different predefined point from the second one.

12. The method as recited in claim 11, wherein a third one of the predefined first point, the predefined second point, the predefined third point, and the predefined fourth point is measured on the basis of the measured results of all preceding predefined points, wherein the third one is a point that is different from both the first one and the second one.

13. The method as recited in claim 1, wherein a third point is measured by the ophthalmological device using a single stimulus.

14. The method as recited in claim 1, wherein a third point is measured by the ophthalmological device using a sequence of stimuli having differing intensities.

15. The method as recited in claim 1, wherein additional measurable points are measured in a first measurement phase following measurement of the at least two predefined points.

16. The method as recited in claim 15, wherein all of the additional measurable points are jointly measured in three further measurement phases, wherein the measured visual field for the eye is derived from the median obtained from the measured results from all measurement phases.

17. The method as recited in claim 15, wherein one optical stimulus having a defined intensity is applied to each predefined point before the first measurement phase, wherein the measurement result is then used to determine an intensity of a subsequent optical stimuli of the first measurement phase.

18. The method as recited by claim 1, wherein the ophthalmological device is a perimeter.

19. The method as recited by claim 1, wherein the at least two predefined points include six predefined points.

20. An ophthalmological device comprising:
(a) a light stimulus apparatus that provides optical stimuli of a defined intensity;
(b) a reaction measuring apparatus that is disposed to measure a reaction by an eye to the optical stimuli provided by the light stimulus apparatus;
(c) an apparatus for processing data that is operably connected with a data base, wherein the data base includes data sets of visual fields, and wherein the ophthalmological device is a perimeter that operates to divide a retina of the eye into points that represent the visual field of the eye, wherein the light stimulus apparatus operates to expose the points of the retina that represent the visual field to optical stimuli of a defined intensity that are provided by the light stimulus apparatus, wherein the apparatus for data processing calculates a reaction to the optical stimuli as a measurement result, wherein at least two predefined points are measured by the perimeter, wherein the at least two predefined points each lie in anatomically independent nerve fibre regions of the eye and are in a statistically significant relation to each other; and the perimeter further operates to derive a measured visual field of the eye from the measurement result calculated by the apparatus for data processing and from the data sets of the data base.

* * * * *